United States Patent [19]
Fujii

[11] Patent Number: 4,718,010
[45] Date of Patent: Jan. 5, 1988

[54] CT SYSTEM FOR CREATING IMAGE DATA FROM HIGH AND LOW ENERGY RADIATION

[75] Inventor: Masashi Fujii, Tokyo, Japan

[73] Assignee: Kabushiki Kaisha Toshiba, Kawasaki, Japan

[21] Appl. No.: 812,892

[22] Filed: Dec. 23, 1985

[30] Foreign Application Priority Data

Dec. 28, 1984 [JP] Japan ............................. 59-276235

[51] Int. Cl.$^4$ .................... G01N 23/04; G01N 23/06; A61B 6/03
[52] U.S. Cl. ....................................... 364/414; 378/5; 378/61
[58] Field of Search ................... 378/5, 61; 364/414

[56] References Cited

U.S. PATENT DOCUMENTS

| | | | |
|---|---|---|---|
| 4,029,963 | 6/1977 | Alvarez et al. | 250/360 |
| 4,217,641 | 8/1980 | Naparstek | 364/414 |
| 4,247,774 | 1/1981 | Brooks | 378/5 X |
| 4,578,803 | 3/1986 | Macovski | 378/62 |
| 4,580,219 | 4/1986 | Pelc et al. | 364/414 |
| 4,590,558 | 5/1986 | Glover et al. | 364/414 |

FOREIGN PATENT DOCUMENTS

| | | |
|---|---|---|
| 0049464 | 4/1982 | European Pat. Off. . |
| 0052394 | 5/1982 | European Pat. Off. . |
| 0052269 | 5/1982 | European Pat. Off. . |
| 0092767 | 11/1983 | European Pat. Off. . |
| 0112487 | 7/1984 | European Pat. Off. . |
| 53-17291 | 2/1978 | Japan . |
| 54-25189 | 2/1979 | Japan . |
| 55-99241 | 7/1980 | Japan . |

Primary Examiner—Jerry Smith
Assistant Examiner—Clark A. Jablon
Attorney, Agent, or Firm—Oblon, Fisher, Spivak, McClelland & Maier

[57] ABSTRACT

A specific slice of a tire is subjected to a high energy radiation which is provided for obtaining projection data of high radiation absorption coefficient portions (steel portions in the tire). The obtained projection data of this steel portions is arranged in a first sinogram. The projection data in this first sinogram is then reconstructed to provide image data. The signal level of the image data is sliced to obtain position data of the steel portions. Based on the obtained position data, the first sinogram for the steel portions is reproduced. This reproduced first sinogram indicates the location of each steel portion. Besides, the same specific slice of the tire is subjected to a low energy radiation which is provided for obtaining projection data of low radiation absorption coefficient portions (rubber portions). The obtained projection data of the rubber portions is arranged in a second sinogram. The second sinogram contains not only the data of the rubber portions, but contains the data of the steel portions. The steel portion data in the first sinogram is subtracted from the corresponding steel portion data in the second sinogram. Then, the subtracted portions in the second sinogram is filled with given data similar to the rubber portion data. Based on the data in this sinogram, image data of the tire is reconstructed.

8 Claims, 9 Drawing Figures

CT SYSTEM FOR CREATING IMAGE DATA FROM HIGH AND LOW ENERGY RADIATION

BACKGROUND OF THE INVENTION

The present invention generally relates to a radiation tomography apparatus for performing tomography of an object under inspection utilizing radiation, and for performing checking/measurement of the object based on the obtained tomographic image.

A computer tomography scanner (hereinafter referred to as a CT apparatus) is known as a typical radiation tomography apparatus. The CT apparatus can non-destructively check for internal defects, composition, structure, etc. of objects, and can perform precise measurement.

The CT apparatus normally has a radiation source and a radiation detector. The radiation source radiates a fan beam X-ray which diverges in a sector plane. The detector is opposite to the radiation source with the object interposed therebetween. The detector has a plurality of radiation sensor elements arranged along the diverging direction of the fan beam X-ray. The radiation source and detector, having the object interposed therebetween, are rotated in one direction in units of degrees within a range of 180 to 360 degrees. Radiation scanning is thus performed. After obtaining X-ray absorption data of an object slice from many directions, processing means, such as a computer, preforms an image reconstruction operation. A tomographic image is then obtained.

In the CT apparatus, for each object slice, an image can be reconstructed with the order of 4,000 gradation steps in accordance with the object composition. From this, the state or condition of the object slice can be inspected in detail.

A CT apparatus as described above is of a so-called third generation CT apparatus. First, second and fourth generation CT apparatuses are also known as other types of the CT apparatus.

A first generation CT apparatus has an X-ray source for generating a pencil beam X-ray and a detector opposed to it. The X-ray source and detector conduct traversal scanning (parallel and straight scanning of X-ray beam) along the slice of an object. Each time one traverse scan is completed, the X-ray source and detector are rotated by a predetermined angle. Thereafter, another traverse scan is similarly performed.

A second generation CT apparatus is an improvement over the first generation CT apparatus. A narrow fan beam X-ray is used in place of the pencil beam X-ray. The detector has only a small number of sensor elements. The X-ray source and detector perform traverse scanning with rotation.

A fourth generation CT apparatus has a detector with sensor elements arranged along the entire circumference of an object, and has an X-ray source for radiating a wide-angle fan beam X-ray. In this apparatus, only the X-ray source is rotated.

In industrial fields, internal defects of products have often be be checked non-destructively. In view of this, the use of a CT apparatus for this purpose has recently been considered promising. FIGS. 1A, 1B and 1C respectively show schematic structures of CT apparatuses of the first, second and third generations. Referring to these figures, reference numeral 1 denotes a radiation source using an X-ray tube or a radioisotope (hereinafter referred to as RI); and 2 denotes a detector. An object to be inspected is placed on table 3 which may be a simple one. Table 3 can be rotated or parallel-shifted so as to allow easy testing and measurement of even large objects.

The first generation CT apparatus in FIG. 1A has radiation source 1 and detector 2 which are fixed opposite each other. Source 1 emits pencil beam radiation B1. Detector 2 has a single sensor element for detecting radiation B1. Table 3 is interposed between source 1 and detector 2. An object (not shown) mounted on table 3 is traversely-scanned in the directions indicated by arrow A. Table 3 is rotated in the direction of arrow B and data is obtained upon completion of each traverse scan.

The second generation CT apparatus shown in FIG. 1B has basically the same construction as FIG. 1A. However, source 1 radiates fan beam radiation B2 in place of pencil beam radiation B1. Detector 2 has a plurality of sensor elements corresponding in number to the spread width of radiation beam B2.

In the third generation CT apparatus shown in FIG. 1C, source 1 generates fan beam radiation B3 having a given spread width which is capable of covering the entire area of table 3. Detector 2 has a plurality of sensor elements corresponding in number to the spread width of radiation B3. Source 1 and detector 2 are fixed and opposite each other with table 3 interposed therebetween. Table 3 is rotated to acquire image data.

Such industrial CT apparatuses conventionally employ X-ray tubes for radiation sources. However, when products of materials having high radiation absorption coefficients or large-sized products are to be checked with X-ray tubes, accurate data being free of noises can be hardly obtained. In such a case, an RI with a high output energy is used.

Assume an object, such as a tire, that contains substances which have both high and low X-ray absorption coefficients, e.g., steel and rubber. If the object is irradiated with X-ray energy suitable for the lower X-ray absorption coefficient substance, the degree of X-ray absorption by the high absorption coefficient substance is too large. The resultant difference between the X-ray absorption of the high coefficient substance and that of the low coefficient substance causes a prominent artifact from the high coefficient substance. This artifact disturbs observation of an image of specific portions having the lower absorption coefficient.

To prevent such artifact, an object may be irradiated with high energy which is well fitted to the higher absorption coefficient. In this case, however, the degree of X-ray attenuation through the substance having the lower X-ray absorption coefficient becomes almost zero. Accordingly, image information of the low absorption coefficient substance is difficult to obtain.

The above problem also applies to a case wherein an RI is used as the radiation source. Theoretically, it is possible to deal with this problem in such a manner that data for steel (high X-ray absorption coefficient) is searched for and extracted from projection data arranged in a sinogram. Then, given interpolated data is put into the specific location of the sinogram, from which the searched data has been extracted. However, it is very difficult to detect the data for steel in a sinogram and, therefore, this manner is hard to actually reduced to practice.

Thus, there is no practically good manner to achieve a precise inspection of the composition of a substance which contains portions (e.g., steel portions and rubber portions) having largely different radiation absorption coefficients.

SUMMARY OF THE INVENTION

It is, accordingly, an object of the present invention to provide a CT apparatus which can measure or inspect the composition of a substance with high resolution, that substance contains portions having largely different radiation absorption coefficients.

Another object of this invention is to provide a method for operating the above CT apparatus.

To achieve the above object, a specific slice of an object (e.g., a tire) to be inspected is subjected to a high energy radiation in a CT apparatus of the invention. This high energy radiation is provided for obtaining projection data of high radiation absorption coefficient portions (e.g., portions formed of steel) in the tire. The obtained projection data of the steel portions is arranged in a sinogram. The projection data in this sinogram is then reconstructed to provide image data. The signal level of the image data is sliced to obtain position data of the steel portions. According to the obtained position data, the sinogram for the steel portions is reproduced. This reproduced steel sinogram indicates the location of each of the steel portions.

On the other hand, the same specific slice of the tire as mentioned above is subjected to a low energy radiation. This low energy radiation is provided for obtaining projection data of low radiation absorption coefficient portions (e.g., portions formed of rubber). The obtained projection data of the rubber portions is arranged in another sinogram (rubber sinogram). This rubber sinogram contains not only the data of the rubber portions, but also contains the data of the steel portions. This steel portion data, which is obtained with the low energy radiation and will cause said artifact, is eliminated from the rubber sinogram.

That is, the steel portion data in the steel sinogram is subtracted from the corresponding steel portion data in the rubber sinogram. Following to this, the subtracted portions in the rubber sinogram is filled with given data which is similar to the rubber portion data. Then, a new sinogram of the tire, which contains the projection data of rubber portions only, is obtained. According to the data in this new sinogram, image data of the tire, which contains only the rubber portions and is free of artifact due to the steel portions, is reconstructed.

DETAILED DESCRIPTION OF THE PREFERRED EMBODIMENTS

The preferred embodiment of the present invention will be described with reference to the accompanying drawings.

Figure 1C:
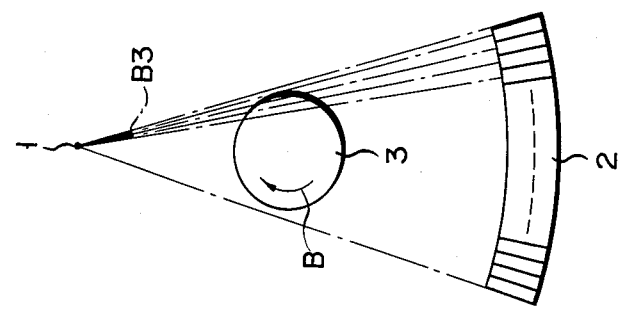
FIGS. 1A to 1C are views for explaining various modes of the CT apparatus according to the present invention.
Figure 1B:
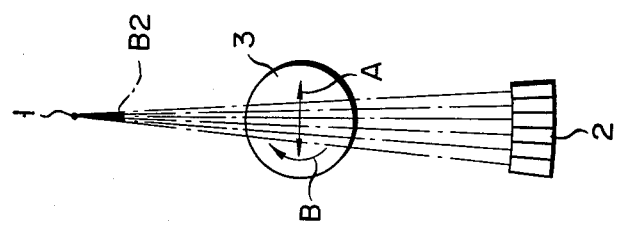
Figure 1A:
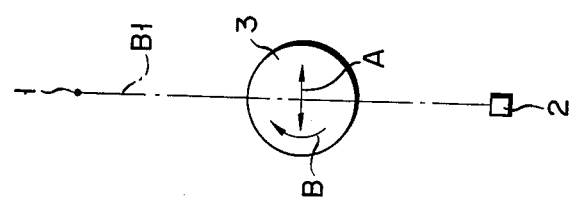

Although a CT apparatus utilizing the present invention may be of any generation type, a third generation CT apparatus as shown in FIG. 1C is adapted to the embodiment, for example.

Figure 2:
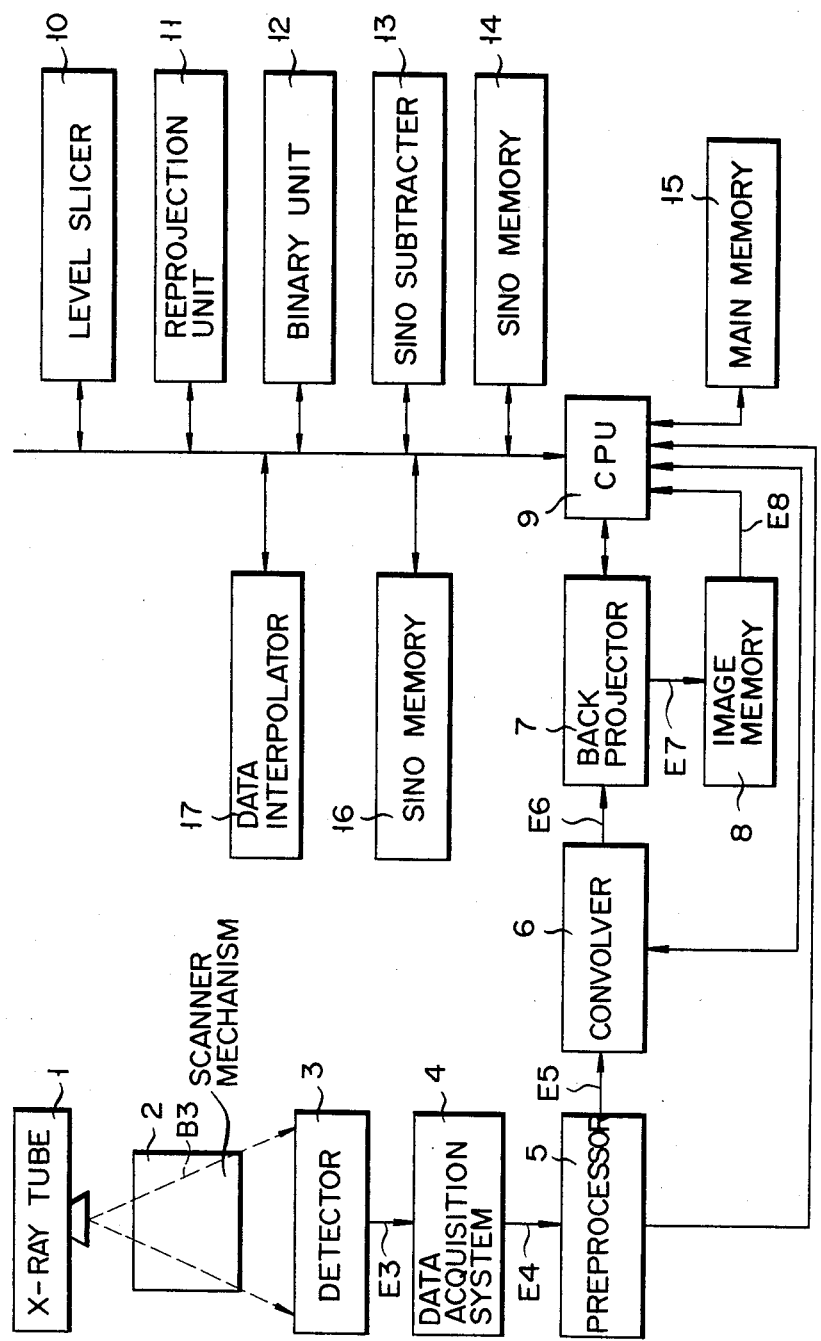
FIG. 2 is a block diagram of an embodiment of the present invention.

FIG. 2 is a block diagram showing the configuration of the above CT apparatus. Referring to FIG. 2, X-ray tube 1 emits fan beam X-ray B3 with a given diverging angle. The operation of tube 1 is controlled by a conventional controller (not shown). Scanner mechanism 2 includes a table (not shown) for holding and rotating an object (not shown) under inspection. Mechanism 2 has a function to rotate and vertically lift the table. Mechanism 2 also has a function to move the table along the central axis of the fan beam X-ray.

X-ray tube 1 is opposed to detector 3 via mechanism 2. Detector 3 is formed of a plurality of radiation sensor elements (not shown) which are arranged with a given fixed pitch along the diverging direction of fan beam B3. These sensor elements are responsive, with a certain spatial resolution, to the intensity of X-ray B3. X-ray absorption data of the object is detected by each radiation sensor element as a current, and the detected current is integrated and converted to voltage signal E3.

Data acquisition system (hereinafter referred to as DAS) 4 independently integrates each signal E3 from the radiation sensor elements in detector 3. DAS 4 converts the integrated signal (E3) into digital data which serves as projection data (X-ray absorption data) E4.

Preprocessor 5 performs preprocessing for each projection data E4 delivered from DAS 4. Preprocessing performed in preprocessor 5 includes logarithmic conversion, gain correction, and offset correction, etc.

Convolver 6 convolves preprocessed data E5 supplied from preprocessor 5. Namely, convolver 6 effects a convolving integration on data E5 by means of a prescribed filter function.

Back projector 7 receives convolved data E6 from convolver 6 and, by back-projecting the convolved data along the projection direction of X-ray B3, reconstructs an image of the object slice in accordance with the contents of data E6.

Memory 8 receives back-projected data E7 from back projector 7 and stores data E7 corresponding to the reconstructed image. CT value (i.e., data representing the degree of the radiation absorption) E8 within a predetermined range is read out from memory 8 and displayed on a CRT display (not shown) with a monochromatic image, for example.

The CT apparatus of FIG. 2 includes processor (CPU) 9 which controls the overall operation of the CT apparatus. Processor 9 is coupled to level slicer 10, reprojection unit 11, binary unit 12, sino subtracter 13 and data interpolator 17. The CT apparatus also includes main memory 15 and sino memories 14 and 16.

Each of sino memories 14 and 16 has a row and column. The combination of the row and column defines a specific address location of the sino memory. The row of the sino memory corresponds to the linear arrangement (channel) of the radiation sensor elements in detector 3. The column of the sino memory corresponds to the rotation angle of the pair of X-ray tube 1 and detector 3. Sino memories 14 and 16 store non-reconstructed projection data. In each of sino memories 14 and 16, a sinogram is formed.

When an X-ray pulse with a predetermined intensity is emitted from X-ray tube 1, data E3 for one-line is obtained from detector 3. Sino data is obtained by linking such one-line data E3 with the address location of the sino memory.

Before starting the operation of the CT apparatus, a tire formed of rubber containing steel (not shown) is mounted on the table of scanner mechanism 2 which is located between X-ray tube 1 and radiation detector 3. When a start instruction is input by an operator to a console (not shown) of the CT apparatus, an X-ray controller (not shown) starts to operate under the control of CPU 9. Then, a high voltage with a given duration is repeatedly applied from a high voltage generator (not shown) to X-rays tube 1, so that tube 1 generates pulsate fan beam X-rays (i.e., the X-ray projection starts).

Each of the pulsate X-ray beams is detected by respective sensor elements of detector 3. The detected X-ray beam are output, in a form of current signals (E3), from detector 3. The current signals derived from respective sensor elements of detector 3 are independently integrated in DAS 4. The integrated current signals (analogs) are A/D (analog to digital) converted and the converted digital signals (E4) are supplied to preprocessor 5. Preprocessed data from preprocessor 5 is supplied to convolver 6.

When complete preprocessed data for one projection is obtained, it is temporarily stored in an image memory, and scanner mechanism 2 rotates its table by a predetermined angle under the control of CPU 9. Subsequently, next X-ray projection starts, and the above-mentioned operation is repeated. In this manner, the step-by-step table rotation and X-ray radiation are alternately repeated to complete data acquisition of the CT image of the tire (object).

When the acquisition of X-ray absorption data of the tire, with respect to the radiation directions from 180 to 360 degrees, is completed, all acquired data is convolved, and the convolved data is back-projected by back projector 7, thereby reconstructing a tomographic image of the tire. This back projecting operation is performed in image memory 8, such that the convolved data is allocated in memory 8 along the arrangement of memory pixels which represents each X-ray beam path of the projecting direction. Then, the allocated data is integrated or accumulated in memory 8 to form a tomographic image of the tire. The complete tomographic image thus obtained is retained in image memory 8.

The operation of the CT apparatus shown in FIG. 2 will be described below with reference to the flow chart of FIG. 3. The object to be inspected may contain two or more kinds of portion shaving various X-ray absorption coefficients. For instance, the object may be a rubber block containing ceramic and steel structure. In the following description, however, a rubber tire containing only steel structure will be used as the object, for the purpose of ease of understanding.

In a first image reconstruction process (ST1-ST7), a specific slice of the tire is subjected to a high energy radiation (ST1). The magnitude of this high energy radiation is determined so that sufficient projection data of the steel structure can be obtained with a good S/N ratio. In the first image reconstruction process, since no projection data of the rubber portion is necessary, the radiation energy may be too high for rubber.

After obtaining projection data of the steel structure, the obtained data is convolved (ST2) and back-projected (ST3) to provide a reconstructed image of the steel structure.

The reconstructed image is binarized or digitized by slicing the CT value (analog) of the reconstructed image at a prescribed threshold level (ST4). This binary digitization is performed by level slicer 10. The binary sliced image includes the information of the steel structure in the tire.

The binary sliced image is temporarily stored in main memory 15. Under the control of CPU 9, the binary image data in memory 15 is sent to sino memory 16 in which the sinogram of the steel structure is reproduced (ST5). For instance, if a certain steel portion is detected by nth radiation sensor element under mth rotation angle of the X-ray radiator-detector pair, the binary image data of this steel portion is stored at the nth row and the mth column of sino memory 16. Thus, the original sinogram arrangement of the projection data of steel is reproduced or reprojected in memory 16. Such a reprojection is performed by the operation of reprojection unit 11 under the control of CPU 9. (The reprojecting operation may be directly performed by CPU 9.) In memory 16, only data of the steel structure is held.

Even when projecting data contains information of a substance (steel) having a high radiation absorption coefficient and of another substance (rubber) having a far smaller radiation absorption coefficient, if a proper threshold level is selected for the binary digitization, projection data regarding only the high radiation absorption coefficient (steel) can be extracted by binary unit 12 (ST6). The extracted binary projection data for steel is then supplied to sino memory 16 (ST7).

After completing the process of steps ST1 to ST7, sino memory 16 holds position data of the steel in the form of a binary image. This position data indicates the location of the steel portions in the tire.

In a second image reconstruction process (ST8-ST15), the specific slice used in the first image reconstruction process (ST1-ST7) is again subjected to a low energy radiation (ST8). In this process, since projection data of the rubber portion is required, the radiation energy should not be too high for rubber. In other words, the radiation energy should be optimum for rubber. The magnitude of this low energy radiation is determined such that even if information of the steel structure is involved in the obtained projection data, optimal projection data of the rubber portion can be obtained. The obtained projection data of the rubber portion is preprocessed, and the preprocessed data is stored in sino memory 14 (ST9).

The arrangement of the sinogram in sino memory 14 (for rubber) is identical to (or corresponding to) that in sino memory 16 (for steel). Projection data regarding the steel structure in memory 14 is erased, by subtraction the steel projection data in memory 16 from the corresponding steel projection data in memory 14. For instance, the steel data stored at address [n, m] of memory 16 is subtracted from the steel data stored at the same address [n, m] (or at the corresponding address [n', m']) of memory 14. This data subtraction with respect to the steel projection data is performed by sino subtractor 13 (ST10).

After performing the above data subtraction, a data-empty portion(s) is produced at a certain memory location(s) in which the steel data has been stored but now it is erased. This data-empty portion of sino memory 14 is filled with prescribed data (ST11). Such data filling is referred to as a "data interpolation" hereinafter. A simple method to achieve the data interpolation is that a digital CT value representing the projection data of the rubber portion is put into the data-empty portion. To be concrete, when the address of the data-empty portion is assume to be [n, m], the average CT value of the rubber data stored in address [(n−1), m] and that in address [(n+1), m] is put into the data-empty portion. Or, the average CT value of data stored in address [(n−1), m], that in address [(n+1), m], that in address [n, (m−1)], and that in address [n, (m+1)], may be used for filling the data-empty portion.

The above data interpolation is effected by interpolator 17. Then, a new sinogram of the tire, which contains the projection data of rubber portions only, is formed in sino memory 14 (ST12). According to the projection data in this new sinogram, image data of the tire, which contains only the rubber portions and is free of artifact due to the steel portions, is reconstructed by convolver 6 and back projector 7 (ST13, ST14). The reconstructed image data of the tire (object) is thus obtained (ST15).

Figure 4:
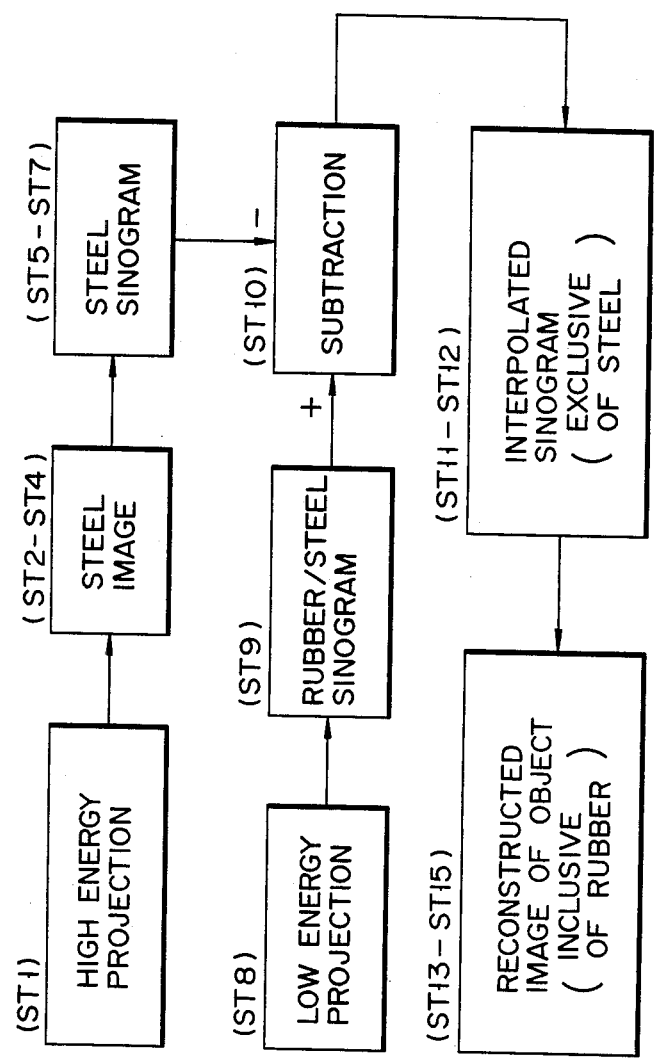
FIG. 4 is a functional block diagram summarizing the flow of FIG. 3.

The above can be summarized as follows. Referring to FIG. 4, a high energy radiation is performed first (ST1), so that steel image data is obtained (ST2-ST4). The obtained steel image data is reprojected so that a sinogram of the steel is reproduced (ST5-ST7). The reprojected steel data is subtracted from other reprojected data (ST10) which is separately prepared with a low radiation energy suitable for rubber (ST8-ST9). The subtracted portion in the sinogram is filled with given rubber data which may be a preselected one or may be one prepared by a proper interpolation (ST11-ST12). Projection data obtained in this manner is used to reconstruct an image of the object containing the rubber portion (ST13-ST15), thereby avoiding an artifact due to the existence of steel.

With this arrangement, adverse influence of a high radiation absorption coefficient steel (i.e., generation of artifact) is practically eliminated, and a reconstructed image with excellent quality can be obtained for a low radiation absorption coefficient rubber.

Figure 3:
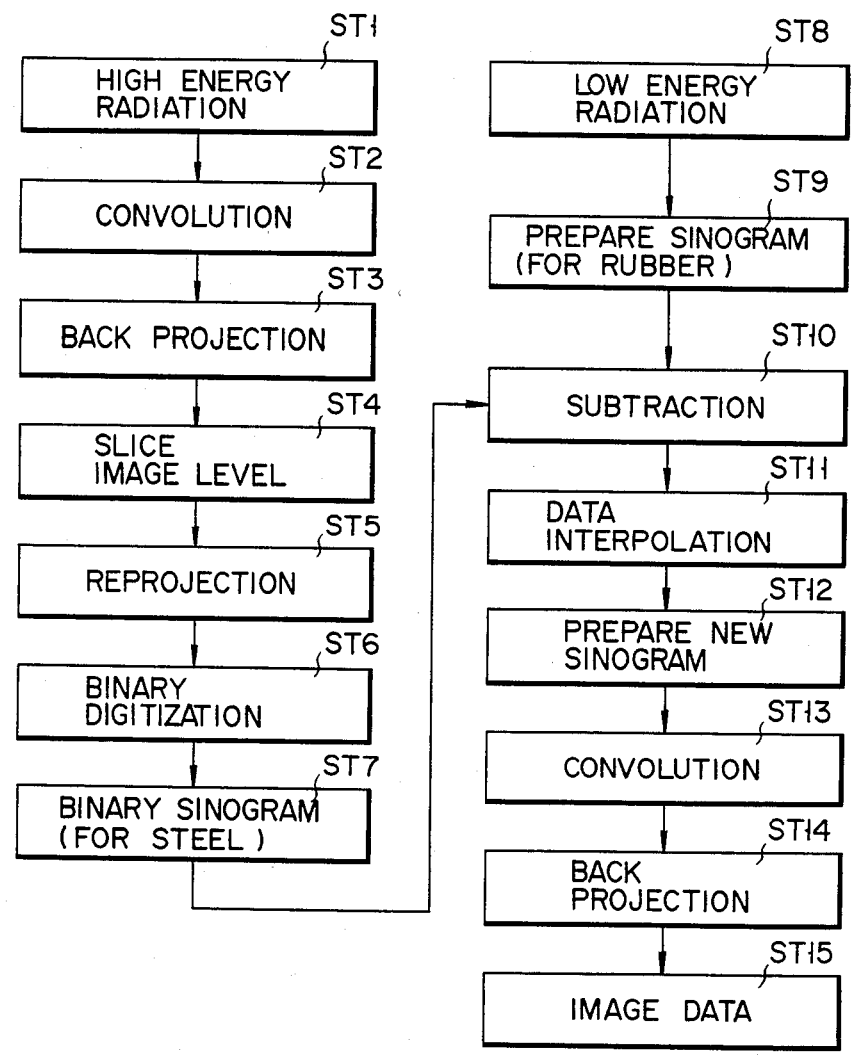
FIG. 3 is a flow chart explaining the mode of operation of the embodiment shown in FIG. 1.
Figure 5:
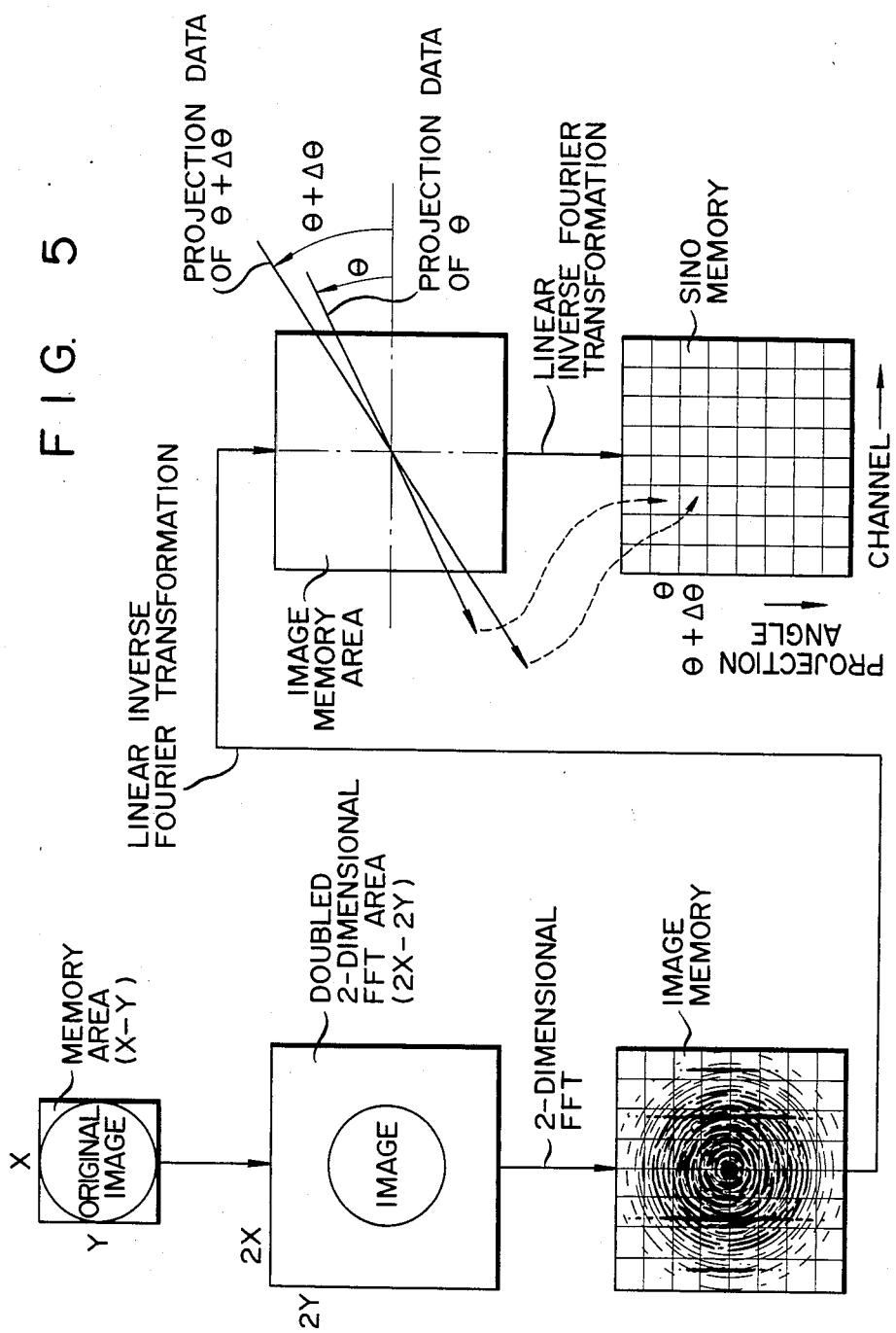
FIG. 5 explains how the reproduction referred to in FIG. 3 is performed.

FIG. 5 explains how the reprojection of step ST5 in FIG. 3 is performed. Assume that the object to be inspected is a circular slice of a tire. As shown in FIG. 5, original image data of the object slice is allocated in the X-Y 2-dimensional area of an image memory. In order to enhance the accuracy of a 2-dimensional fast Fourier transformation (FFT), the X-Y area of the image memory is doubled, so that the FFT is effected in the 2X-2Y 2-dimensional area.

The transformed object slice data obtained by the FFT is arranged in an image memory. The data arranged in the 2X-2Y area of the image memory is rearranged in a polar coordinate by means of a linear inverse Fourier transformation. The projection data with respect to projection angle $\theta$ in this polar coordinate is sampled by each radiation sensor element of detector 3 shown in FIG. 2. Then, the sampled data is stored in the row of angle $\theta$ and in the column of each channel of a sino memory. Similarly, the projection data with respect to projection angle $\theta + \Delta\theta$ is sampled and stored in the row of angle $\theta + \Delta\theta$ and in the column of each channel of the sino memory. In this manner, the projection data of all projection angle in the polar coordinate is sampled and stored in the sino memory, and the reprojection of the object slice is completed.

Figure 6:
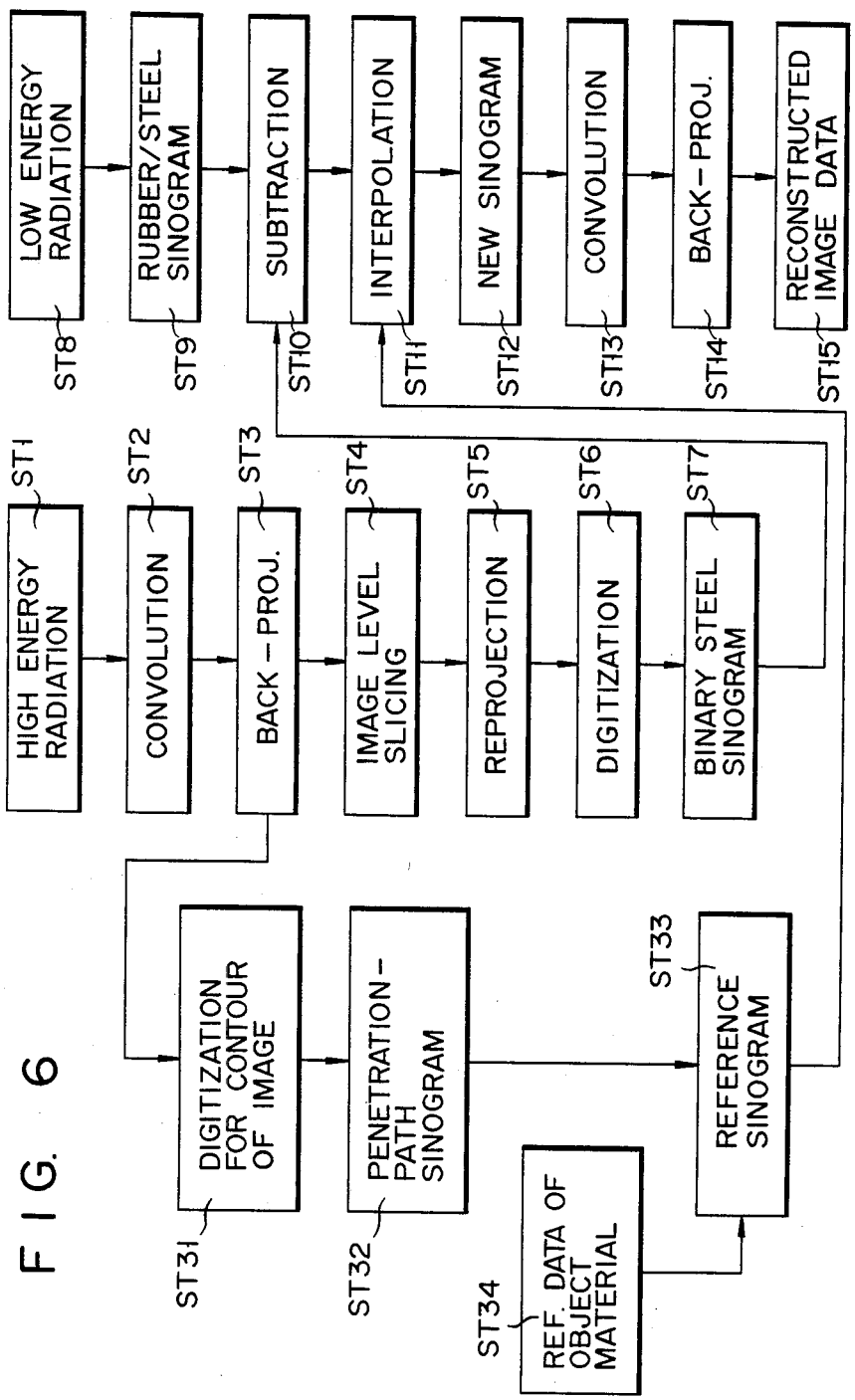
FIG. 6 is a flow chart explaining the mode of other operation of the embodiment shown in FIG. 1.
Figure 7:
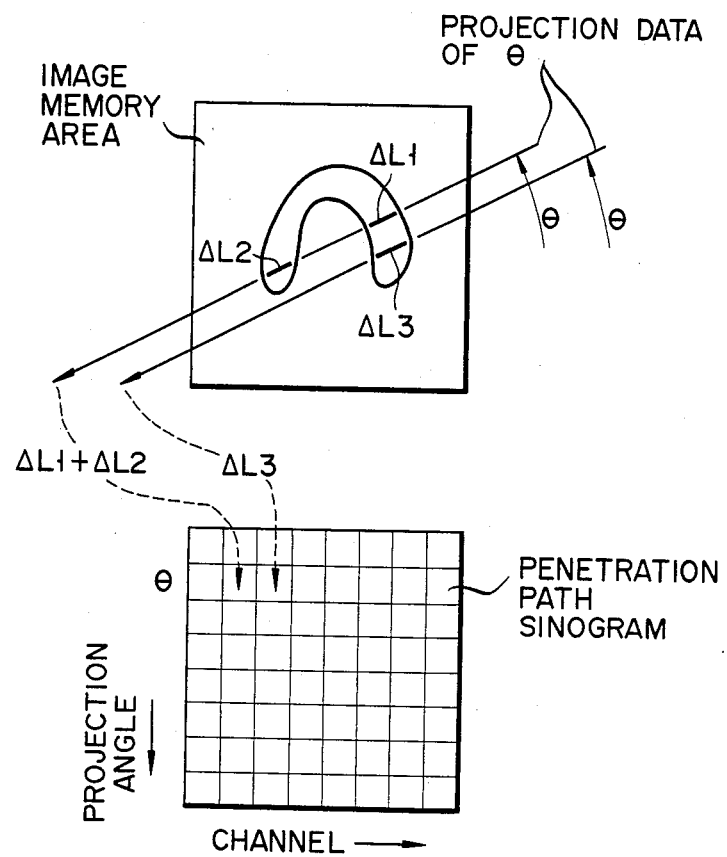
FIG. 7 illustrates how the penetration-path sinogram is prepared.

FIG. 6 is a flow chart which is a modification of the flow shown in FIG. 3. FIG. 6 differs from FIG. 3 in that new steps ST31-ST34 are specially provided in the flow of FIG. 6. FIG. 7 illustrates how the penetration-path sinogram of step ST32 is prepared.

After completing the back-projection for the contour of the tire (ST3), the contour of the tire image data is digitized (ST31). The digitizing operation of step ST31 may be similar to that of step ST6. This contour data is arranged in a polar coordinate formed in the image memory area (FIG. 7). Image data ($\Delta L1 + \Delta L2$, $\Delta L3$, etc.) of angle $\theta$ detected by respective radiation sensor elements (channels), which represents the penetration path of the radiation, is arranged in a penetration-path sinogram (ST32). The data in the penetration-path sinogram indicates the thickness of the tire in the object slice.

A given projection data value for the tire thickness is put into each position of the tire thickness in the penetration-path sinogram, so that a reference sinogram is prepared (ST33). This given projection data value may be predetermined one that has been obtained before the operation-start of the flow of FIG. 6 (ST34). For instance, an actually measured projection data value of the tire portion of the object (tire) may be used as the given projection data value. The reference sinogram thus obtained is used for interpolating (ST11) the sino data delivered from subtracting step ST10.

Incidentally, if data to be interpolated represents a bulky portion in the object slice, the flow of FIG. 6 is suitable to effectively eliminate unfavorable artifact.

As has been described above, according to the present invention, it is possible to provide a CT apparatus which can display a high-resolution image without artifact even for an object having substances with both high and low radiation absorption coefficients.

The present invention need not be limited to the particular embodiment described above and illustrated in the accompanying drawings. Various changes or modifications may be made within the scope of the present invention as claimed. For instance, assume a case wherein the object to be inspected is a rubber block (low X-ray absorption coefficient) containing ceramic (medium X-ray absorption coefficient) and steel (high X-ray absorption coefficient) structures, and the ceramic structure is to be inspected without artifact due to the steel structure. In this case, a medium energy radiation, which is suitable for ceramic, is used in the step of ST8 (FIGS. 3 or 6). The finally obtained image data (ST15) includes the image of ceramic only. This is because the intensity of the medium energy radiation is too high for rubber so that the CT value of the rubber portion is substantially zero, while the projection data of the steel portion is eliminated by the subtraction step ST10. If the steps of ST1-ST7 in FIG. 3 is not used and a high energy radiation, which is suitable for steel, is used in the step of ST8, the finally obtained image data (ST15) includes the image of steel only. This is because the intensity of the high energy radiation is too high both for rubber and ceramic.

What is claimed is:

1. A CT apparatus in which radiation rays are radiated from a radiation ray source in many directions for each slice of an object under inspection, in which projection data of the object slice is detected and acquired, with a given spatial resolution, by a radiation detector, and in which an image of the object slice is reconstructed from the acquired projection data, comprising:

first reconstruction means, coupled to said radiation detector, for reconstructing an image of a high radiation absorption coefficient substance from projection data obtained by a high energy radiation, and providing reconstructed image data of said high radiation absorption coefficient substance;

first sino means, coupled to said first reconstruction means, for producing first image data of said high radiation absorption coefficient substance from said reconstructed image data, and reproducing a first sinogram of said high radiation absorption coefficient substance from said first image data, wherein data in said first sinogram indicates the location of said high radiation absorption coefficient substance in the object slice;

inspection means, coupled to said radiation detector, for inspecting said object slice with a low energy radiation, and providing second image data corresponding to projection data of a low radiation absorption coefficient substance;

second sino means, coupled to said inspection means, for reproducing a second sinogram of said low radiation absorption coefficient substance from said second image data, wherein data in said second sinogram indicates the location of the high and low radiation absorption coefficient substances in the object slice, and the location or arrangement of data in said second sinogram corresponds to that in said first sinogram;

elimination means, coupled to said first sino means and second sino means, for eliminating data of said first sinogram from data, which corresponds in position to the first sinogram data, of said second sinogram, and providing new projection data; and second reconstruction means, coupled to said elimination means, for reconstructing an image of said object slice in accordance with said new projection data.

2. A CT apparatus according to claim 1, wherein said second reconstruction means includes:

interpolation means, coupled to said elimination means, for interpolating said new projection data by predetermined data which is similar to the data of said low radiation absorption coefficient substance, such that the data eliminated portion in said second sinogram is filled with said predetermined data.

3. A CT apparatus according to claim 2, wherein said second reconstruction means further includes:

third sino means, coupled to said interpolation means, for reproducing a third sinogram of said low radiation absorption coefficient substance from the interpolated new projection data; and means, coupled to said third sino means, for reconstructing the image of said object slice from the data in said third sino means.

4. A CT apparatus according to claim 2, wherein said interpolation means includes:

contour means, coupled to said first reconstruction means, for binary digitizing the contour of the reconstructed image of sai dhigh radiation absorption coefficient substance to provide contour data which indicates the position of said high radiation absorption coefficient substance;

reference data means for providing reference data whose value represents the CT value of said low radiation absorption coefficient substance; and reference sinogram means, coupled to said contour means and said reference data means, for reproducing said predetermined data in a reference sinogram whose arrangement corresponds to the arrangement of said second sinogram, the location of said predetermined data in said reference sinogram being defined by said contour data, and the CT value thereof being defined by said reference data.

5. A CT apparatus according to claim 1, wherein said reconstructed image data has a given CT value, and said first sino means includes:

slicer means for slicing, at a predetermined threshold level, the CT value of said reconstructed image data to produce said first image data.

6. A CT apparatus according to claim 5, wherein said first sino means further includes:

reprojection means, coupled to said slicer means, for reprojecting said firs timage data to provide reprojected data;

binary means, coupled to said reprojection means, for binary digitizing said reprojected data to provide binary reprojected data; and sinogram means, coupled to said binary means, for reproducing said first sinogram in accordance with said binary reprojected data.

7. An operating method for a CT apparatus in which radiation rays are radiated from a radiation ray source in many directions for each slice of an object under inspection, in which projection data of the object slice is detected and acquired, with a given spatial resolution, by a radiation detector, and in which an image of the object slice is reconstructed from the acquired projection data, said operating method comprising the steps of:

(a) subjecting the object slice to a high energy radiation which is provided for obtaining projection data of high radiation absorption coefficient portions, and arranging the obtained projection data of said high radiation absorption coefficient portions in a first sinogram;

(b) reconstructing the arranged projection data in said first sinogram to provide first image data;

(c) slicing a signal level defined by said first image data to obtain position data of said high radiation absorption coefficient portions;

(d) reprojecting the position data of said high radiation absorption coefficient portions to reproduce said first sinogram;

(e) subjecting said object slice to a low energy radiation which is provided for obtaining projection data of low radiation absorption coefficient portions;

(f) arranging the obtained projection data of said low radiation absorption coefficient portions in a second sinogram, said second sinogram containing not only the data of said low radiation absorption coefficient portions, but also containing the data of said high radiation absorption coefficient portions, the location or arrangement of data in said second sinogram corresponding to that in said first sinogram;

(g) eliminating the data in said first sinogram from the corresponding data in said second sinogram;

(h) filling the subtracted data portion in said second sinogram with given data; and (i) constructing the arranged projection data in said second sinogram to provide image data of said object slice.

8. An operating method according to claim 7, wherein said given data for filling the subtracted data portion corresponds to the projection data of said low radiation absorption coefficient portions.

* * * * *